United States Patent [19]

Dudley et al.

[11] Patent Number: 4,891,239

[45] Date of Patent: Jan. 2, 1990

[54] METHOD AND APPARATUS FOR ULTRAFAST MICROWAVE TISSUE FIXATION

[75] Inventors: Kenneth W. Dudley, Sudbury; Wesley W. Teich, Wayland; John S. Sklenak, Sudbury, all of Mass.

[73] Assignee: Raytheon Company, Lexington, Mass.

[21] Appl. No.: 339,908

[22] Filed: Apr. 13, 1989

Related U.S. Application Data

[63] Continuation of Ser. No. 215,168, Jul. 5, 1988, abandoned.

[51] Int. Cl.[4] .......................... A01G 5/06; A01N 1/00; A61N 1/00; H05B 6/64
[52] U.S. Cl. ......................................... 427/4; 128/804; 219/10.55 A; 219/10.55 M; 427/45.1
[58] Field of Search ................ 128/804; 219/10.55 A, 219/10.55 M; 427/4, 45.1

[56] References Cited

PUBLICATIONS

"Ultrafast Microwave Energy Fixation for Electron Microscopy"; Journal of Histochemistry & Cytochemistry; vol. 34, No. 3; 1986; pp. 381–387.
"H2500 Microwave Processor/Stainer"; BIO-RAD Microscience Div.; Cambridge, Mass.
"Microwave Irradiator for Experimental Animals", NJE2603-10KW, New Japan Radio Co., Ltd., 1984.
"Toshiba 5 and 10 KW Microwave Fixation Systems", Stoelting Co., Chicago, Ill.
"Toshiba Microwave Applicator", Muromachi Kikai Co., Ltd., (plus English translation—Stoelting Co., Chicago, Ill.

*Primary Examiner*—Michael Lusignan
*Attorney, Agent, or Firm*—Steven C. Stewart; William R. Clark; Richard M. Sharkansky

[57] ABSTRACT

A method and apparatus for ultrafast microwave tissue fixation using a single mode resonant waveguide constructed with an aperture near one end. The waveguide is also constructed to provide a uniform E field and maximum power field below the aperture. Tissue is placed into a vial filled with fixation solution. The vial and tissue are then inserted through the aperture into the waveguide. Microwave energy is then applied to the tissue which becomes fixated within a short period of time.

36 Claims, 2 Drawing Sheets

METHOD AND APPARATUS FOR ULTRAFAST MICROWAVE TISSUE FIXATION

This application is a continuation of application Ser. No. 215,168 filed July 5, 1988, now abandoned.

BACKGROUND OF THE INVENTION

This invention relates generally to tissue fixation and more particularly to tissue fixation in a waveguide with a magnetron generating radio frequency energy therein.

As is well known, pathologists diagnose diseases by examining tissue samples from biopsies or other similar medical procedures. Because it is important that the cells be examined in a state as close to the living state as possible, the tissue samples are typically put through a chemical fixation process in order to stop the cells from degrading. More specifically, the samples are typically immersed in a preserving solution which commonly includes formaldehyde. The solution penetrates the walls of the cells, hardens the cell structure and thereafter prevents or greatly retards further degradation. Subsequently, a pathologist subjects the sample to various tests and examinations for diagnosis.

One significant problem of the above-described fixation process is that it takes a relatively long period of time, such as, for example, eight hours, for the preserving solution to penetrate the cell walls. Accordingly, the fixation process may prevent a relatively fast diagnosis. Also, at least during the early stages of fixation, the cells continue to degrade. This delay may cause the cells to change from their original living state, and, in some cases, may cloud the diagnosis.

In the prior art, it has been found that microwave energy speeds up the penetration of the preserving solution into cells. More specifically, in order to speed up the fixation process, submersed tissue samples have been placed in multimodal microwave ovens. When a multimode oven is used, the specimen is placed in a vial with a formaldehyde solution and then placed within a microwave oven cavity. The microwave oven is then powered on for a period of one to two minutes. For reasons not fully understood but apparently related to the vibration of molecules, the presence of the microwave field greatly increases the rate at which the fixation solution penetrates the cell walls. For example, the microwave field may reduce a typical fixation process from several hours down to about 1 minute.

The method of fixating cells using a multimode microwave oven has presented certain disadvantages. A multimode cavity has wide dispersion of microwave energy. This dispersity results in the specimen being heated in a non-uniform manner, thereby causing the specimen to have hot or cold spots. In some cases, cells in hot spots will be destroyed and cells in cold spots will not become fixated.

In addition, using a multimode microwave oven presents the problem of an inconsistency of results every time the microwave oven is used. A multimode microwave oven has the fields constantly changing throughout the oven. These changes cause a different heat pattern within the specimen each time the specimen is fixated. Inconsistency of fixation causes errors in analysis because the pathologist needs a stable baseline in which to make his diagnosis.

Other problems with a multimode oven include requiring the use of a very high power magnetron. In a multimode cavity, microwave energy is spread over a large area. This dispersion of microwave energy may result in a low concentration of energy being distributed to the specimen. Accordingly, to get a high concentration into the specimen requires a high power microwave energy source.

It has also been observed that when the specimen or sample touches the side of a vial during fixation in a microwave single mode cavity, hot spots develop on the sample at the point where the sample touches the vial. These hot spots could destroy the specimen and cause invalid diagnosis when the specimen is looked at under a microscope.

Also, if there is any moisture on a vial in a single mode microwave cavity, the vial may be subject to cracking when exposed to higher power microwave energy.

Finally, using a microwave oven to fixate cells causes problems with the amount of exposure to the cell. In a typical microwave oven, the cell exposure time that can only be adjusted on a second-to-second basis. During fixation, it is sometimes desirable to expose the cell to a specified length of time accurate to within one-hundredth of a second.

SUMMARY OF THE INVENTION

An objective of this invention is to provide an improved apparatus for fixating tissue.

An objective of this invention is to provide a tissue fixation device that provides a uniform energy field throughout the tissue being fixated.

Another object of this invention is to accurately control the microwave energy absorbed by the tissue being fixated.

Another object of this invention is to provide an apparatus that can precisely adjust the duration of the radio frequency energy across the tissue being fixated.

Also an object of this invention is to provide an apparatus that transmits the majority of the microwave energy from the microwave energy source and transmits that energy across the tissue being fixated.

Another object of this invention is to provide a method for testing the microwave cavity to determine where to position the tissue to be fixated in order to maximize the power going into the tissue.

A further object of this invention is to provide an apparatus that removes moisture from the vial to prevent the vial from cracking when the vial is subjected to microwave energy.

Another primary objective of this invention is to provide an apparatus that fixates tissue in a consistent manner from sample to sample.

These and other objects are provided in accordance with the invention, which defines an apparatus for fixating tissue comprising means for holding the tissue submerged in a fixating solution; a waveguide having a cavity with a first section, a second section and a transitional section formed therebetween, the waveguide having an opening at one end and a wall at the other end; means for transmitting radio frequency energy through the opening into the first and the second section; an aperture disposed within the waveguide for inserting the tissue holding means within the second cavity, the aperture being positioned on the waveguide to cause a substantially uniform E field of the radio frequency energy through the tissue holding means when inserted; and impedance matching means, disposed within the second section for providing impedance within the waveguide wherein minimal microwave energy is reflected back to the transmitting means. It may be preferable that the apparatus for fixating tissue further comprise means for adjusting the length that the tissue holding means protrudes into the second section so as to finally adjust the radio frequency energy reflection within the waveguide. It may also be preferable that the apparatus further comprise means for choking microwave energy escaping through the aperture from the waveguide. It may be further be preferable that the apparatus for fixating tissue further comprise means for preventing moisture or ionized gas from collecting on the tissue holding means. Alternately, the apparatus for fixating tissue may comprise test means for measuring the amount of microwave energy reflected in the waveguide; and circular means, disposed between the microwave generating means and the waveguide for distributing microwave energy from the microwave generating means into the cavity and distributing reflected energy from the cavity to the test means. It may be preferable that the tissue holding means includes a vial. It may also be preferable that the vial contains means, disposed adjacent the inside perimeter of the vial, for preventing the tissue from touching the sides of the vial. It may preferable that the waveguide is single mode resonant.

The invention may be further practiced by a method of fixating tissue comprising the steps of: placing the tissue to be fixated into a fixation solution in a vial, placing the vial into a waveguide having a first and second section formed therein, providing radio frequency energy into the waveguide such that substantially uniform E field forms through the vial, and providing an impedance within the second section wherein minimal microwave energy is reflected back to the transmitting means. It may be preferable that the fixating of tissue comprise the step of adjusting the length that the vial protrudes into the second section, so as to finally adjust the matching impedance within the waveguide. The method of fixating tissue may further comprise the step of: preventing microwave energy from escaping from where the vial is inserted into the waveguide. The method of fixating tissue may also comprise the step of preventing moisture from collecting on the vial outer surface. The method of fixating tissue may further comprise the steps of suspending tissue in the center of the vial and preventing the tissue from touching the sides of the vial. Also, the method of fixating tissue may comprise the step of adjusting the duration of radio frequency energy into the waveguide. Alternately, the method of fixating tissue may comprise the steps of providing a lower power level radio frequency energy to the vial, measuring the reflected power of the radio frequency energy, and adjusting the length the tissue holding means protrudes into the second section, so as to reduce the reflected power level.

BRIEF DESCRIPTION OF THE DRAWINGS

The foregoing objects and advantages will be more fully understood by reading the Description of the Preferred Embodiments with reference to the drawings wherein.

DESCRIPTION OF THE PREFERRED EMBODIMENTS

Figure 2:
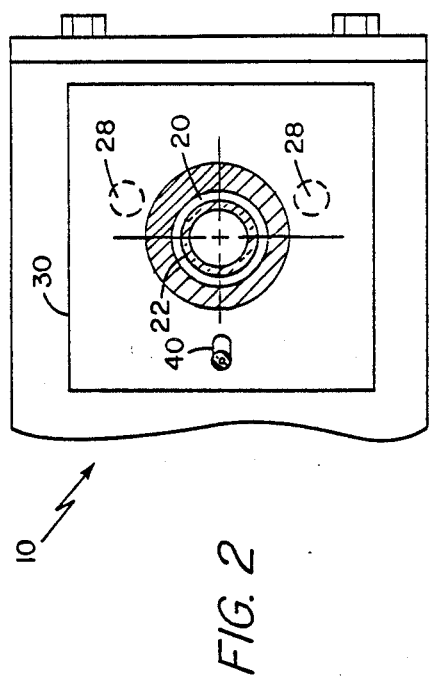
FIG. 2 is a top view taken along line 2—2 in FIG. 1.
Figure 1:
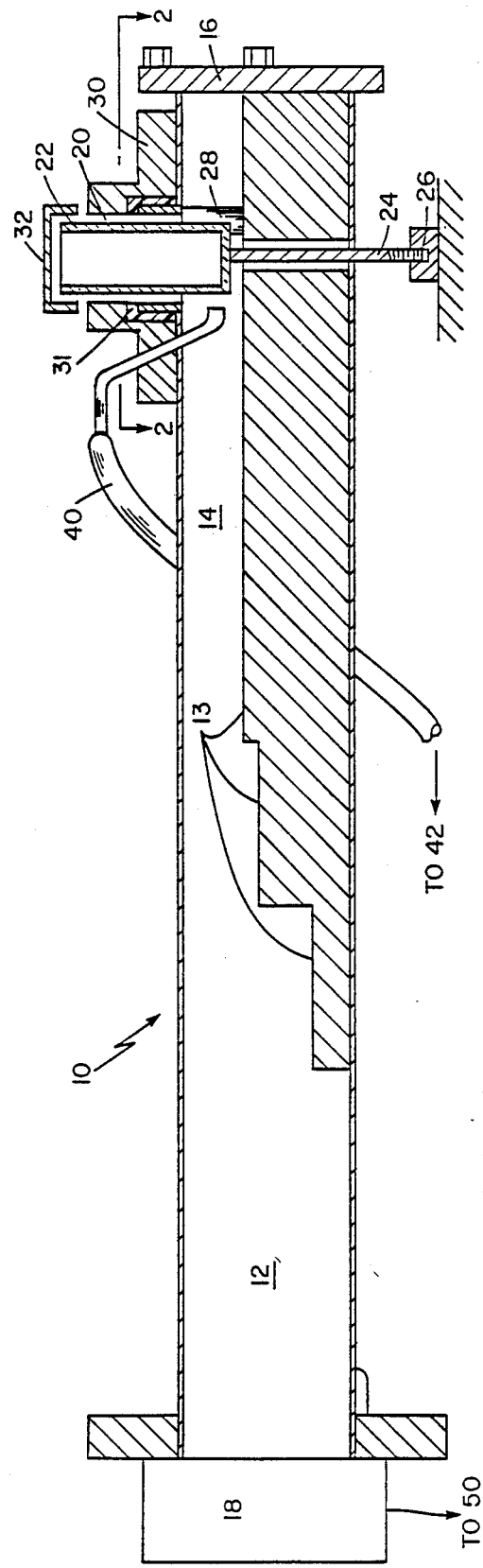
FIG. 1 is a sectioned view of the fixation device of the present invention.

Referring now in detail to the drawings and particularly to FIGS. 1 and 2 thereof, there is shown an illustration of a single-mode resonant waveguide embodying features of the present invention, generally designated by the reference numeral 10. However, a full height cavity could be easily substituted.

The waveguide 10 having a width of 2.5-4.5 inches and a height of 1.25-2.3 inches generally includes a first section 12 and a transitional section having one or more steps 13 leading up to a second section 14. The steps shown have increments of 0.3 to 1.0 inches. At one end of waveguide 10 bordering second section 14 is wall 16. The other end of waveguide 10 is connected to magnetron 18. Typically, magnetron 18 has a power of 0.5 to 5.0 KW and generates the microwave energy into the waveguide 10. Although many microwave frequencies will be suitable for this apparatus, the preferable frequencies are 2.450 GHz and 915 MHz. These preferable frequencies are the ones approved by the FCC for microwave oven operation.

The dimensions given for FIGS. 1 and 2 are for one exemplary waveguide that has a magnetron 18 generating microwave energy at a frequency of 2.450 GHz.

On the top surface of waveguide 10 above second section 14 is aperture 20 having a diameter of approximately ⅞". Second section 14 has a reduced height, relative to first section 12, of 0.7 inches. Inserted into aperture 20 is a removable glass vial 22. Glass vial 22 is supported by post 24 which is screwed into vernier adjustment or tuner 26. Center of aperture 20 is positioned on waveguide 10 approximately one-quarter (2.450 GHz) wavelength from wall 16 to provide a uniform field through glass vial 22 when glass vial 22 is inserted into aperture 20 and second cavity 14.

Also disposed within second section 14 between glass vial 22 and wall 16 are inductive posts 28. Inductive posts 28 are positioned in second section 14 behind the aperture 20, approximately 1.5" from the wall 16 and approximately 1.3" from the sides of waveguide 10. Inductive posts 28 maximizes the E field through glass vial 22 and minimizes reflection to magnetron 18 (see FIG. 2).

Disposed adjacent waveguide 10 over second section 14 is choke 30. Choke 30 has a slot 31 with an opening positioned a quarter wavelength (1.7 inches for 2.450 GHz) above the top of waveguide 10 to prevent microwave energy from leaving waveguide 10. During operation, vial 22 is inserted into aperture 20 within choke 30. If vial 22 is made of a glass, plastic or ceramic material, microwave energy will not escape from waveguide 10 through aperture 20.

Disposed on top of choke 30 is metal cover 32. Metal cover 32 may be used to provide added safety from microwave energy leakage. Also, metal cover 32 prevents any spattering of solution 34 in vial 22 from escaping from waveguide 10.

Figure 4:
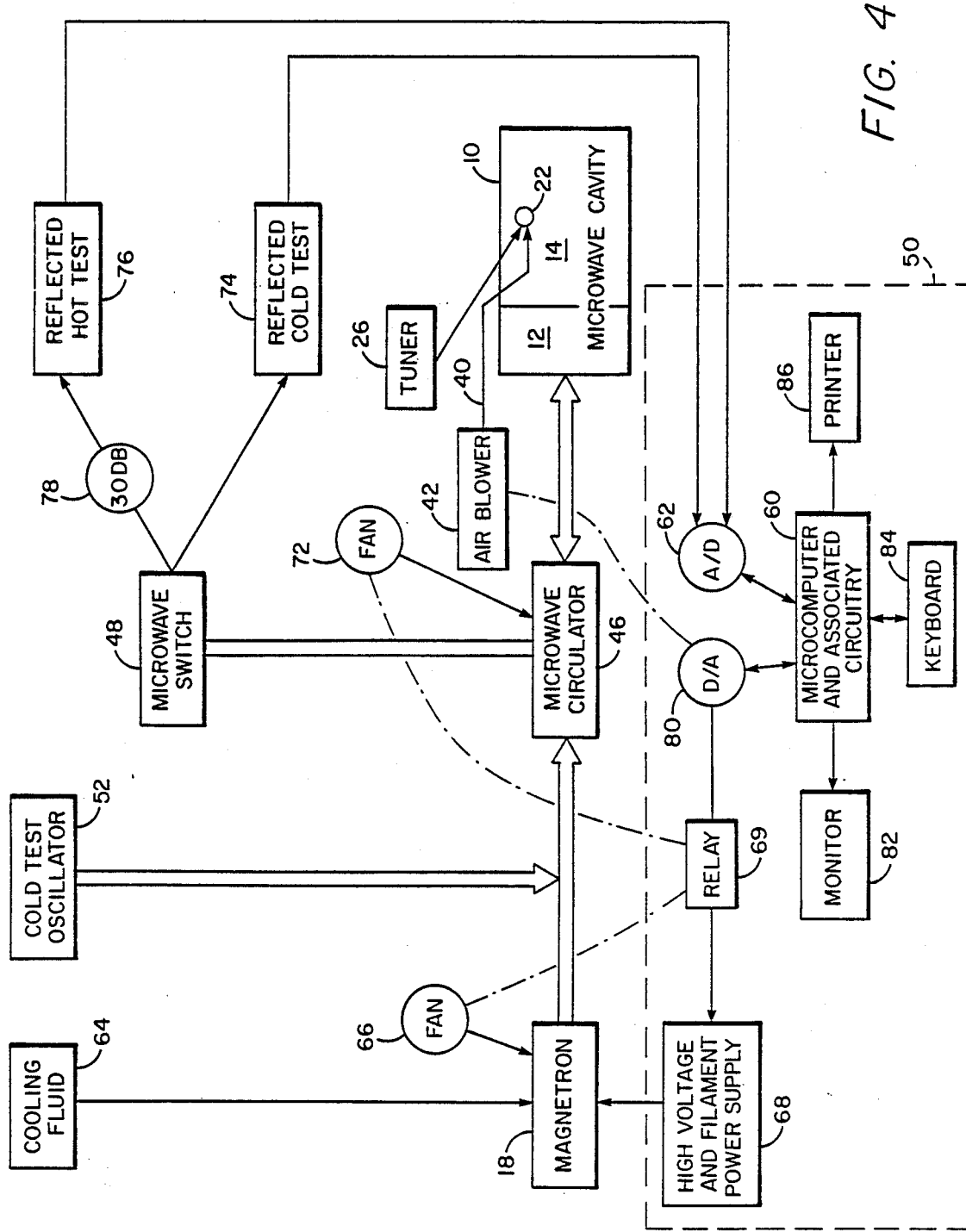
FIG. 4 is a diagram of an alternate embodiment of the fixation device using a microwave circulator and a test device.

Optionally, coupled to waveguide 10 between glass vial 22 and magnetron 18 is air duct 40. Coupled to air duct 40 outside waveguide 10 is blower 42 (FIG. 4). Blower 42 provides nitrogen or other gas to glass vial 22 to remove moisture or any ionized gas from gathering on or around glass vial 22 when magnetron 18 is operating. The blower 42 is preferably a tank of nitrogen gas which is turned on during operation. By preventing moisture from gathering in front of glass vial 22, both a greater E field is provided throughout glass vial 22 and arcing is prevented around glass vial 22. Arcing could cause glass vial 22 to crack.

Coupled to magnetron 18 is control device 50 (FIG. 4). Control device 50 energizes magnetron 18. Control device 50 comprises a microcomputer 60 (FIG. 4) coupled to a relay 69 (FIG. 4) which is then coupled to the power supply 68 (FIG. 4). The relay 69 internally connects power supply to magnetron 18 to energize magnetron 18. By having a microcomputer 60 control the relay 69 (FIG. 4) connect time, the time period that magnetron 18 is turned on can be accurately and precisely controlled. This time period can range from one-hundredth of a second to several minutes. Further, the control device 50 can make the turn on time of magnetron 18 accurate to 0.001 seconds.

Figure 3:
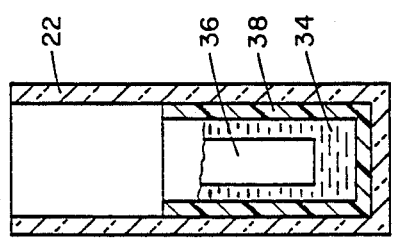
FIG. 3 is a sectioned view of the vial shown in FIG. 1.

Referring to FIG. 3, there is shown the glass vial 22 used in waveguide 10 that holds sample 36. This vial 22 is typically made from a glass, a ceramic material or a plastic material. To prepare a vial 22, formaldehyde preserving solution 34 is placed in the vial 22. The sample 36 is then inserted into vial 22 and submerged in the solution 34. Optionally, open cell foam 38 may be inserted along the inside perimeter of glass vial 22. The foam 38 rests along the inside perimeter of glass vial 22. Though the fixation process may be done without foam 38, foam 38 provides a mechanism for preventing sample 36 from touching the sides of glass vial 22. Sample 36 touching the glass vial 22 during fixation operation could create hot spots within sample 36. The thickness of foam 38 is typically one-sixteenth to one-eighth of an inch.

To prepare a sample using foam 38, first the glass vial 22 is filled with foam 38 along the inside perimeter and bottom of glass vial 22. Formaldehyde preserving solution 34 is then placed in vial 22 and finally sample 36 is then placed in the vial 22. The vial 22 is then placed in waveguide 10 through aperture 20 such that the sample 36 is disposed below the top surface of waveguide 10 and in second section 14.

During operation, the control device 50 turns on magnetron 18 which energizes waveguide 10 with microwave energy. The magnetron 18 is turned on between 0.01 and 2 seconds depending on the size of the sample 36 and the power of the magnetron 18. Typically for a 2KW magnetron 18 and a 2 cc sample size power is applied for 75 ms. When magnetron 18 is energized, microwave energy travels down waveguide from first section 12 to second section 14. Second section 14 provides an impedance match to minimize reflection in the waveguide 10. Further, the geometry of the waveguide is set up to provide maximum power transfer into the sample, thereby providing controlled heating. Also, using single mode waveguide 10 (rather than a multimode microwave oven) to fixate a sample 36, the fixation process time can be reduced from minutes to milliseconds.

Vernier adjustment or tuner 26, which is connected to member 44, may be turned to adjust the distance that vial 22 protrudes through aperture 20 into second section 14. This tuner 26 finely tunes the E field within vial 22 to minimize the reflection, thereby maximizing energy to the sample 36 and maximizing the fixation rate.

Referring to FIG. 4, shown is a block diagram of an alternate embodiment of the apparatus with a waveguide 10 having a magnetron 18, a microwave circulator 46, cold test oscillator 52, microwave switch 48 and control device 50. This configuration provides for low-level testing using cold test oscillator 52 to reduce reflection in waveguide 10 before the magnetron 18 is powered on.

Waveguide 10 has a first section 12 and second section 14 and a tuner 26 as shown in FIG. 1. Magnetron 18 supplies energy in waveguide 10. Connected to magnetron 18 is cooling fluid 64 and fan 66 to prevent magnetron 18 from overheating. Supplying power to magnetron 18 is a high voltage filament power supply 68. Connected to power supply 68 is relay 69. Relay 69 enables and disables power supply 68.

Cold test oscillator 52 is connected to circulator 46 and provides a lower power source (milliwatt) to test waveguide 10. Circulator 46 distributes energy to waveguide 10 from cold test oscillator 52 and magnetron 18. Circulator 46 is cooled by fan 72. Circulator 46 has three ports. The first ports is connected to waveguide 10. The second ports is connected to magnetron 18 and cold test oscillator 52. The third ports of the circulator 46 is connected to a matching microwave load. A sample probe is inserted into the load, taps a small amount of the reflected power and sends it to switch 48.

Microwave switch 48 connects microwave circulator 46 to a reflected cold test channel 74 and to a reflected hot test channel 76. Hot test channel 76 and cold test channel 74 are each connected to a separate crystal detector (not shown) which is connected to A/D converters 62 within control device 50. Between microwave switch 48 and the reflected hot test channel 76 is a 30 dB attenuator 78 that reduces power into the hot test channel 76 to prevent overheating of the A/D converter 62. Microwave switch 48 deflects microwave energy from waveguide 10 into reflected hot test channel 76 and a reflected cold test channel 74.

Within control device 50 is microcomputer and associated circuitry 60, an A/D converter 62, a D/A converter 80, relay 69 and power supply 68. Microcomputer 60 is connected to A/D converter 62 to process the results of the reflected cold test and reflected hot tests. Microcomputer 60, via relay 69, turns the fans 66 and 72 off and on. Microcomputer 60 via D/A converter 80 regulates the stream of nitrogen to the glass vial 22 with an electrically controlled solenoid (not shown) connected between air duct 40 and air blower 42. Microcomputer 60 also monitors the temperature within the vial 22 with a temperature probe (not shown). After microwave irradiation, the vial is lifted up to allow insertion of the temperature probe.

Connected to microcomputer 60 within control device 50 is a D/A converter 80, a monitor 82, a keyboard 84 and a printer 86. D/A converter 80 connects to relay 69 to allow microcomputer 60 to control power to magnetron 18, fan 66 and fan 72. D/A converter 80 has a variable level set by microcomputer 60. The output from D/A converter 80 is raised to a predetermined voltage level which energizes relay 69 resulting in power flowing to power supply 68, fan 66 and fan 72. Monitor 82 displays the results of all testing and provides a human interface for the user to control the fixation device. Keyboard 84 allows for the user to set the parameters of the testing. Printer 86 allows a recording of test results. Depending on the results of the test, waveguide 10 is finely tuned by tuning vernier adjustment post 26 to provide a minimum amount of reflection, as previously described.

During operation, the glass vial 22 is filled with about 2 cc of solution 34 and sample 36. The vial 22 is then inserted into waveguide 10, as previously described in connection with FIG. 3. The cold test oscillator 52 is then turned on, which sends microwave energy through circulator 46 and into waveguide 10. The microwave energy then reflects off of back wall 16 and into circulator 46. The reflected microwave energy is then distributed to microwave switch 48 which sends that energy to reflected cold test channel 74 where the energy is coupled to A/D converter 62. The energy level is then read by microcomputer 60. If microcomputer 60 determines that the reflected energy is too large, tuner 26 is then turned to reduce the amount of the reflection.

After the low-level test has been completed, the magnetron 18 is enabled by microcomputer 60, which turns on power supply 68. Once power supply 68 is turned on, magnetron 18 then turns on, and sends high power microwave energy into waveguide 10 via circulator 46. Microwave energy is then transmitted down waveguide 10 and into glass vial 22. The sample then fixates in the formaldehyde solution 34, as previously described in connection with FIG. 3.

The reflection of microwave energy in waveguide 10 is distributed into the matching load and probe within microwave circulator 46. The energy is then distributed to microwave switch 48, through 30 dB attenuator 78 and into hot test channel 76. The A/D converter 62 then samples the signal in the hot test channel 76. The microcomputer 60 then reads the value of A/D converter 62 and prints the value of the reflection amplitude. The reflection amplitude value can be saved within the microcomputer's associated circuitry 60 for later retrieval.

Because of the uniformity of the E field and the accuracy of the power on time, the same fixation result is obtained from sample to sample. This consistency provides a stable baseline for the pathologist to do quality testing and obtain similar results.

Having described preferred embodiments of this invention, it is now evident that other embodiments incorporating these concepts may be used. It is felt, therefore, that this invention should not be restricted to the disclosed embodiments, but should be limited only by the spirit and scope of the appended claims.

What is claimed is:

1. An apparatus for fixating tissue comprising:
   means or holding said tissue submerged in a fixating solution;
   a waveguide having a cavity formed therein with a first section, a second section, and a transition section formed therebetween, said waveguide having an opening at one end and a wall at the other end;
   means for transmitting radio frequency energy through said opening and into said cavity;
   an aperture disposed within said waveguide for inserting said tissue holding means within said second section, said aperture being positioned on said waveguide to cause a substantially uniform E field of said radio frequency energy through said tissue in said tissue holding means when inserted; and
   an inductive post disposed within said second section adjacent said aperture, said post being positioned between said aperture and said wall.

2. The apparatus for fixating tissue as recited in claim 1 further comprising:
   means for adjusting the length that said tissue holding means protrudes into said second so as to finely adjust the radio frequency energy reflection within said waveguide.

3. The apparatus for fixating tissue as recited in claim 1 further comprising:
   means for choking microwave energy escaping through said aperture from said waveguide.

4. The apparatus for fixating tissue as recited in claim 1 further comprising:
   means for preventing moisture or any ionized gas from collecting on said tissue holding means.

5. The apparatus for fixating tissue as recited in claim 1 further comprising:
   test means for measuring the amount of microwave energy reflected in said waveguide; and
   circulator means, disposed between said microwave generating means and said waveguide, for distributing microwave energy from said microwave generating means into said cavity and distributing reflected energy from said cavity to said test means.

6. The apparatus for fixating tissue as recited in claim 1 wherein said tissue holding means includes a vial.

7. The apparatus for fixating tissue as recited in claim 1 wherein said waveguide contains a plurality of inductive posts.

8. The apparatus for fixating tissue as recited in claim 6 wherein said vial contains means, disposed adjacent the inside perimeter of said vial, for preventing said tissue from touching the sides of said vial.

9. The apparatus as recited in claim 8 wherein said preventing means is disposed adjacent the bottom of said vial.

10. The apparatus for fixating tissue as recited in claim 8 wherein said foam is 0.01 to 0.3 inches thick.

11. The apparatus as recited in claim 1 wherein said waveguide is single mode resonant.

12. The apparatus as recited in claim 1 wherein said second section forms a reduced height waveguide.

13. The apparatus as recited in claim 1 wherein said waveguide has a width of 2.5–4.5 inches and a height of 1.25–2.3 inches.

14. The method of fixating tissue in a waveguide having an aperture and a cavity with a first and second section formed therein, said cavity having a transitional section formed between said first and second section, said cavity having an opening at one end and a wall at the other end, comprising the steps of:
   placing the tissue to be fixated into a fixation solution in a vial;
   placing the vial into said aperture;
   providing radio frequency energy into said waveguide such that substantially uniform E field forms through said vial; and
   providing a conductive post within said cavity second section adjacent said aperture, said post being positioned between said aperture and said wall.

15. The method of fixating tissue as recited in claim 14 further comprising the step of adjusting the length that said vial protrudes into said aperture so as to finely adjust the reflection of said radio frequency energy within said waveguide.

16. The method of fixating tissue as recited in claim 14 further comprising the step of preventing microwave energy from escaping from said aperture.

17. The method of fixating tissue as recited in claim 14 further comprising the step of preventing moisture from collecting on said vial outer surface.

18. The method of fixating tissue as recited in claim 14 further comprising the steps of suspending tissue in the center of said vial and preventing said tissue from touching the sides of said vial.

19. The method of fixating tissue as recited in claim 14 comprising the step of adjusting the duration of radio frequency energy into said waveguide.

20. The method of fixating tissue as recited in claim 14 further comprising the steps of:
   providing a lower power level radio frequency energy to said vial;
   measuring the reflected power level of said radio frequency energy; and
   adjusting the length said tissue holding means protrudes into said aperture so as to reduce said reflected power level.

21. An apparatus for fixating tissue comprising:
   a vial containing tissue submerged in a fixating solution;
   a single mode resonant waveguide having a cavity formed therein with a first section, a second section, and a transitional section formed therebetween, said waveguide having an opening at one end and a wall at the other end;
   means for transmitting radio frequency energy through said opening into said cavity;
   an aperture disposed within said waveguide for inserting said vial within said second section, said aperture being positioned on said waveguide a quarter wavelength of said radio frequency energy from said wall to cause a substantially uniform E field of said radio frequency energy through said vial when inserted; and
   an inductive post, disposed within said second section between said aperture and said wall and modifying impedance within said waveguide so that minimal microwave energy is reflected back to said transmitting means.

22. Apparatus as recited in claim 20 wherein said second section has a reduced height relative to said first section.

23. Apparatus as recited in claim 21 further comprising a veneer adjustment post protruding into said second section and supporting said vial, said post having a means for adjusting the length said post protrudes into said cavity so as to finely adjust the amount of radio frequency energy hitting said sample.

24. Apparatus as recited in claim 21 further comprising means disposed adjacent the inside perimeter of said vial for preventing said tissue from touching the sides of said vial.

25. Apparatus as recited in claim 23 further comprising means, having an air duct and a blower for preventing moisture or ionized gas from collecting on said outside of said vial by blowing gas on said vial when said vial is in said second section.

26. The apparatus as recited in claim 21 wherein said waveguide has a width of 2.5-4.6 inches and a height of 1.25-2.3 inches.

27. The apparatus as recited in claim 1 wherein said aperture is positioned a quarter wavelength of said radio frequency energy from said wall.

28. An apparatus for fixating tissue comprising:
   means for holding tissue submerged in a fixating solution, said tissue holding means having an outside surface;
   a waveguide having a cavity formed therein, said waveguide having an opening at one end and a wall at the other end;
   means for transmitting radio frequency energy through said opening and into said cavity;
   an aperture disposed within said waveguide for inserting said tissue holding means into said waveguide; and
   means for preventing moisture or any ionized gas from collecting on the outside surface of said tissue holding means.

29. The apparatus as recited in claim 28 wherein said tissue holding means is a glass or ceramic vial.

30. The apparatus as recited in claim 28 wherein said preventing means includes an air duct and a gas source that blows gas on said tissue holding means.

31. The apparatus as recited in claim 28 wherein said vial contains means, disposed adjacent the inside perimeter of said vial, for preventing said tissue from touching the sides of said vial.

32. An apparatus for fixating tissue comprising:
   means for holding tissue submerged in a fixating solution;
   a waveguide having a cavity, said waveguide having an opening at one end and a wall at the other end;
   means for transmitting radio frequency energy through said opening and into said cavity;
   an aperture disposed within said waveguide for inserting said tissue holding means within said cavity, said aperture being positioned on said waveguide so that a substantially uniform E field of said radio frequency energy occurs in said tissue when said tissue holding means is inserted; and
   an inductive post, disposed within said cavity and adjacent said aperture.

33. The apparatus as recited in claim 32 wherein said post is disposed between said aperture and said wall.

34. The method of fixating tissue in a microwave waveguide having a cavity comprising the steps of:
   placing the tissue to be fixated in a fixation solution in a vial;
   placing the vial into said cavity;
   providing radio frequency energy into said waveguide such that a substantially uniform E field forms through said vial; and
   providing a conductive post within said cavity adjacent said vial.

35. The method as recited in claim 34 wherein said cavity has a wall at one end and a cavity at the other end; and wherein said conductive post is disposed between said aperture and said wall.

36. The method of fixating tissue in a waveguide having a cavity formed therein comprising the steps of:
   holding tissue substantially submerged in a fixating solution within a vial;
   placing said vial in said waveguide cavity;
   transmitting said radio frequency energy in said waveguide; and
   preventing said tissue from touching the sides of said vial.

* * * * *